United States Patent [19]

Spencer et al.

[11] Patent Number: 5,688,880

[45] Date of Patent: Nov. 18, 1997

[54] READILY SUPPORTABLE METAL COMPLEXES

[75] Inventors: Lee Spencer, Pearland, Tex.; Peter N. Nickias, Midland, Mich.

[73] Assignee: The Dow Chemical Company, Midland, Mich.

[21] Appl. No.: 570,262

[22] Filed: Dec. 11, 1995

[51] Int. Cl.$^6$ ...................................................... C08F 4/643
[52] U.S. Cl. .................. 526/127; 526/130; 526/134; 526/160; 526/943; 502/103; 502/117; 502/120; 502/152; 556/11; 556/52; 556/53; 556/13; 556/19; 556/28; 534/15
[58] Field of Search ......................... 534/15; 556/11, 556/52, 53; 502/103, 117, 120, 152; 526/127, 130, 134, 160, 943

[56] References Cited

U.S. PATENT DOCUMENTS 5,475,075 12/1995 Brant et al. ......................... 526/348.3
5,556,928 9/1996 Devore et al. ...................... 526/127

*Primary Examiner*—Mark Nagumo

[57] ABSTRACT

Metal complexes useful as olefin polymerization catalysts corresponding to the formula:

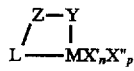

wherein:

L is a delocalized, π-bonded group that is bound to M, containing up to 50 nonhydrogen atoms;

M is a metal of Group 3, 4 or the Lanthanide series of the Periodic Table of the Elements;

Z is a covalently bound, divalent substituent of up to 50 non-hydrogen atoms having the formula, $-(ER_2)_m-$, wherein E independently each occurrence is carbon, silicon or germanium, R independently each occurrence is selected from the group consisting of $C_{1-20}$ hydrocarbyl, and $C_{1-20}$ hydrocarbyloxy, with the proviso that in at least one occurrence R is $C_{1-20}$ hydrocarbyloxy, and m is an integer from 1 to 3;

Y is a divalent ligand group comprising nitrogen, phosphorus, oxygen or sulfur, said Y containing up to 20 nonhydrogen atoms;

X' is a neutral Lewis base ligand having up to 20 non-hydrogen atoms;

X" independently each occurrence is a monovalent, anionic moiety selected from hydride, halo, hydrocarbyl, silyl, germyl, hydrocarbyloxy, amide, siloxy, halohydrocarbyl, halosilyl, silylhydrocarbyl, and aminohydrocarbyl having up to 20 non-hydrogen atoms, or two X" groups together form a divalent hydrocarbadiyl group;

n is a number from 0 to 3; and p is an integer from 0 to 2.

12 Claims, No Drawings

READILY SUPPORTABLE METAL COMPLEXES

This invention relates to metal complexes and to addition polymerization catalysts formed therefrom that have improved catalytic performance, especially when supported on aluminum or silicon containing supports. More particularly such complexes comprise one or more Group 3, 4, or Lanthanide metal complexes containing one or more hydrocarboxy substituted silane bridging groups. In addition, the present invention relates to the process for preparing supported derivatives of such complexes and to a method of using such complexes as one component of a polymerization catalyst in an addition polymerization process for polymerizing addition polymerizable monomers.

In U.S. Ser. No. 545,403, filed Jul. 3, 1990, (published in equivalent form Mar. 13, 1991 as EP-A-416,815) there are disclosed certain constrained geometry metal complexes and catalysts derived by reacting the metal complex with activating cocatalysts. Supported derivatives of such catalysts were prepared by contacting them with a support such as alumina, silica or $MgCl_2$. In U.S. Pat. No. 5,064,802 (published Mar. 20, 1991 in equivalent form as EP-A-418, 044) there are disclosed certain further catalysts formed by reacting metal complexes with ion forming activating cocatalysts that are salts of Bronsted acids containing a noncoordinating compatible anion. The reference discloses the fact that such complexes are usefully employed as catalysts in addition polymerizations. In U.S. Ser. No. 876, 268, filed May 1, 1992 (published in equivalent form Dec. 30, 1992 as EP-A-520,732) an alternative technique for preparing cationic constrained geometry catalysts using borane activators is disclosed.

In U.S. Pat. No. 4,892,851 there are disclosed biscyclopentadienyl Group 4 metal complexes, especially complexes of zirconium or hafnium that are usefully employed with alumoxane activating cocatalysts for use in addition polymerizations, especially the polymerization of aliphatic α-olefins. In a series of patents, W. Spaelick has disclosed certain ring substituted stereorigid bisindenyl complexes and their use as olefin polymerization catalysts. The bridging group of such complexes generically includes silicon, germanium or tin containing divalent groups containing hydride, halogen, $C_{1-10}$ alkyl, $C_{1-10}$ fluoroalkyl, $C_{6-10}$ aryl, $C_{6-10}$ fluoroaryl, $C_{1-10}$ alkoxy, $C_{2-10}$ alkenyl, $C_{7-40}$ aralkyl, $C_{8-40}$ aralkenyl or $C_{7-40}$ alkylaryl groups or ring forming combinations thereof. Such disclosure may be found in U.S. Pat. Nos. 5,243,001, 5,145,819, 5,304,614, 5,350,817, among others. For the teachings contained therein, the foregoing United States patents and applications are herein incorporated by reference.

It would be desirable if there were provided an improved catalyst system that is more readily adaptable to forming supported catalyst systems as well as an improved addition polymerization process utilizing such catalyst systems.

SUMMARY OF THE INVENTION

As a result of investigations carried out by the present inventors there have now been discovered new and improved Group 3, 4, or Lanthanide metal complexes corresponding to the formula:

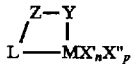

or a dimer, solvated adduct, chelated derivative or mixture thereof, wherein:

L is a delocalized, π-bonded group that is bound to M, containing up to 50 nonhydrogen atoms;

M is a metal of Group 3, 4 or the Lanthanide series of the Periodic Table of the Elements;

Z is a covalently bound, divalent substituent of up to 50 non-hydrogen atoms having the formula, $—(ER_2)_m—$, wherein E independently each occurrence is carbon, silicon or germanium, R independently each occurrence is selected from the group consisting of $C_{1-20}$ hydrocarbyl, and $C_{1-20}$ hydrocarbyloxy, with the proviso that in at least one occurrence R is $C_{1-20}$ hydrocarbyloxy, and m is an integer from 1 to 3;

Y is a divalent ligand group comprising nitrogen, phosphorus, oxygen or sulfur, said Y containing up to 20 nonhydrogen atoms;

X' is a neutral Lewis base ligand having up to 20 non-hydrogen atoms;

X" independently each occurrence is a monovalent, anionic moiety selected from hydride, halo, hydrocarbyl, silyl, germyl, hydrocarbyloxy, amide, siloxy, halohydrocarbyl, halosilyl, silylhydrocarbyl, and aminohydrocarbyl having up to 20 non-hydrogen atoms, or two X" groups together form a divalent hydrocarbadiyl group;

n is a number from 0 to 3; and p is an integer from 0 to 2.

There are also provided improved catalyst compositions comprising one or more of the foregoing Group 3, 4 or Lanthanide metal complexes and one or more activating cocatalysts.

In a further embodiment there is provided a supported catalyst system comprising one or more of the foregoing metal complexes, on or more activating cocatalysts, and an aluminum or silicon containing support material.

Finally there is provided an improved method for polymerization of addition polymerizable monomers using one or more of the above addition polymerization catalysts or catalyst systems. Such addition polymerization processes may be used to prepare polymers for use in molding, film, sheet, extrusion foaming and other applications.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Suitable L groups for use herein include any neutral or anionic π-electron containing moiety capable of forming a delocalized bond with the Group 3, 4 or Lanthanide metal. Examples of such neutral groups include arene moieties such as benzene, anthracene or naphthalene, as well as substituted derivatives of such groups. Examples of anionic π-electron containing moieties include allyl, pentadienyl, cyclopentadienyl, cyclohexadienyl, as well as substituted derivatives of such groups.

By the term "derivative" when used to describe the above substituted, delocalized π-bonded groups is meant that each atom in the delocalized π-bonded group may independently be substituted with a radical selected from the group consisting of hydrocarbyl radicals, halo-, cyano or dialkylamino- substituted-hydrocarbyl radicals, and hydrocarbyl-substituted metalloid radicals wherein the metalloid is selected from Group 14 of the Periodic Table of the Elements. Suitable hydrocarbyl and substituted-hydrocarbyl radicals used to form derivatives of the substituted, delocalized π-bonded group will contain from 1 to 20 carbon atoms and include straight and branched alkyl radicals, cycloalkyl radicals, aryl radicals, alkyl-substituted cycloalkyl radicals, and alkyl-substituted aromatic radicals. In addition two or more such radicals may together form a fused ring system or a hydrogenated fused ring system. Examples of the latter are indenyl-, tetrahydroindenyl-, fluorenyl-, and octahydrofluorenyl-groups. Suitable hydrocarbyl-substituted organometalloid radicals include mono-, di- and trisubstituted organometalloid radicals of Group 14 elements wherein each of the hydrocarbyl groups contains from 1 to 20 carbon atoms. More particularly, suitable hydrocarbyl-substituted organometalloid radicals include trimethylsilyl, triethylsilyl, ethyldimethylsilyl, methyldiethylsilyl, triphenylgermyl, trimethylgermyl and the like.

Preferred L groups are anionic L groups, including, cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and $C_{1-10}$ hydrocarbyl-substituted derivatives thereof. Most preferred anionic L groups are tetramethylcyclopentadienyl, 2-methylindenyl, 3-methylindenyl and 2,3-dimethylindenyl.

Examples of highly preferred complexes according to the present invention correspond to the formula:

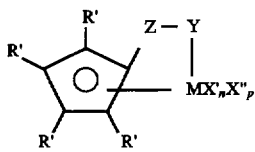

wherein:
M is titanium, zirconium or hafnium, preferably titanium, in the +2, +3 or +4 formal oxidation state;
—Z—Y— is as previously defined;
R' independently in each occurrence is selected from the group consisting of hydrogen, hydrocarbyl, silyl, germyl, cyano, halo and combinations thereof, said R' having up to 20 non-hydrogen atoms each, or adjacent R' groups together form a divalent derivative that is a hydrocarbadiyl, siladiyl or germadiyl group;
X' is a conjugated diene having from 4 to 30 non-hydrogen atoms, which forms a π-complex with M when M is in the +2 formal oxidation state, whereupon n is 1 and p is 0;
X" each occurrence is an anionic ligand group that is covalently bonded to M when M is in the +3 or +4 formal oxidation state, whereupon n is 0 and p is 1 or 2, and optionally two X" groups together form a divalent anionic ligand group.

Preferably, R' independently in each occurrence is selected from the group consisting of hydrogen, methyl, ethyl, and all isomers of propyl, butyl, pentyl and hexyl, as well as cyclopentyl, cyclohexyl, norbornyl, benzyl, and trimethyl silyl; or adjacent R' groups are linked together thereby forming a fused ring system such as an indenyl, 2-methylindenyl, 3-methylindenyl, 2,3-dimethylindenyl, 2-methyl-4-phenylindenyl, 2-methyl-4-naphthylindenyl, tetrahydroindenyl, fluorenyl, tetrahydrofluorenyl, or octahydrofluorenyl group.

Preferred L groups include cyclopentadienyl, tetramethylcyclopentadienyl, indenyl, tetrahydroindenyl, fluorenyl, tetrahydrofluorenyl, octahydrofluorenyl, or one of the foregoing groups further substituted with one or more methyl, ethyl, propyl, butyl, pentyl, hexyl, (including branched and cyclic isomers), norbornyl, benzyl, or phenyl groups.

Examples of suitable X' moieties include: $\eta^4$-1,4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; and $\eta^4$-1,4-bis(trimethylsilyl)-1,3-butadiene. Of the foregoing 1,4-diphenyl-1,3-butadiene, 1-phenyl-1,3-pentadiene, and 2,4 hexadiene are preferred.

Examples of suitable X" moieties include chloride, methyl, benzyl, phenyl, tolyl, t-butyl, methoxide, and trimethylsilyl or two X" groups together are 1,4-butanediyl, s-cis(1,3-butadiene), or s-cis(2,3-dimethyl-1,3-butadiene).

Preferred Z groups are those wherein E is silicon, m is 1, and R in at least one occurrence is methoxide, ethoxide, propoxide or butoxide.

Preferred Y groups are amido groups of the formula —NR*—, wherein R* is $C_{1-10}$ hydrocarbyl, especially methyl, ethyl, propyl, butyl, pentyl, hexyl, (including branched and cyclic isomers), norbornyl, 2, 4, 6-trimethylphenyl, adamantanyl, benzyl, or phenyl.

In the most preferred embodiment —Z—Y— is an amidosilane or amidoalkane group of up to 10 nonhydrogen atoms, especially, (tert-butylamido) (2-butoxymethylsilanediyl), (tert-butylamido) (isopropoxymethylsilanediyl) or (tert-butylamido) (ethoxymethylsilanediyl).

Illustrative derivatives of Group 3, 4 or Lanthanide metals that may be employed in the practice of the present invention include:

2-butoxymethylsilanediyl complexes (n-butylamido)2-butoxymethyl($\eta^5$-tetramethylcyclopentadienyl)silanetitanium (II) 1,4-diphenyl-1,3-butadiene, (n-butylamido)2-butoxymethyl($\eta^5$-tetramethylcyclopentadienyl)silanetitanium (II) 1,3-pentadiene, (n-butylamido)2-butoxymethyl($\eta^5$-tetramethylcyclopentadienyl)silanetitanium (III) 2-(N,N-dimethylamino)benzyl, (n-butylamido)2-butoxymethyl($\eta^5$-tetramethylcyclopentadienyl)silanetitanium (IV) dimethyl, (n-butylamido)2-butoxymethyl($\eta^5$-tetramethylcyclopentadienyl)silanetitanium (IV) dibenzyl, (cyclododecylamido)2-butoxymethyl($\eta^5$-tetramethylcyclopentadienyl)silanetitanium (II) 1,4-diphenyl-1,3-butadiene, (cyclododecylamido)2-butoxymethyl($\eta^5$-tetramethylcyclopentadienyl)silanetitanium (II) 1,3-pentadiene, (cyclododecylamido)2-butoxymethyl($\eta^5$-tetramethylcyclopentadienyl)silanetitanium (III) 2-(N,N-dimethylamino)benzyl, (cyclododecylamido)2-butoxymethyl($\eta^5$-tetramethylcyclopentadienyl)silanetitanium (IV) dimethyl, (cyclododecylamido)2-butoxymethyl($\eta^5$-tetramethylcyclopentadienyl)silanetitanium (IV) dibenzyl, (2,4,6-trimethylanilido)2-butoxymethyl($\eta^5$-tetramethylcyclopentadienyl)silanetitanium (II) 1,4-diphenyl-1,3-butadiene, (2,4,6-trimethylanilido)2-butoxymethyl($\eta^5$-tetramethylcyclopentadienyl)silanetitanium (II) 1,3-pentadiene, (2,4,6-trimethylanilido)2-butoxymethyl($\eta^5$-tetramethylcyclopentadienyl)silanetitanium (III) 2-(N,N-dimethylamino)benzyl,
(2,4,6-trimethylanilido)2-butoxymethyl($\eta^5$-tetramethylcyclopentadienyl)silanetitanium (IV) dimethyl,
(2,4,6-trimethylanilido)2-butoxymethyl($\eta^5$-tetramethylcyclopentadienyl)silanetitanium (IV) dibenzyl,
(1-adamantylamido)2-butoxymethyl($\eta^5$-tetramethylcyclopentadienyl)silanetitanium (II) 1,4-diphenyl-1,3-butadiene,
(1-adamantylamido)2-butoxymethyl($\eta^5$-tetramethylcyclopentadienyl)silanetitanium (II) 1,3-pentadiene,
(1-adamantylamido)2-butoxymethyl($\eta^5$-tetramethylcyclopentadienyl)silanetitanium (III) 2-(N,N-dimethylamino)benzyl,
(1-adamantylamido)2-butoxymethyl($\eta^5$-tetramethylcyclopentadienyl)silanetitanium (IV) dimethyl,
(1-adamantylamido)2-butoxymethyl($\eta^5$-tetramethylcyclopentadienyl)silanetitanium (IV) dibenzyl,
(n-butylamido)2-butoxymethyl($\eta^5$-2-methylindenyl)silanetitanium (II) 1,4-diphenyl-1,3-butadiene,
(n-butylamido)2-butoxymethyl($\eta^5$-2-methylindenyl)silanetitanium (II) 1,3-pentadiene,
(n-butylamido)2-butoxymethyl($\eta^5$-2-methylindenyl)silanetitanium (III) 2-(N,N-dimethylamino)benzyl,
(n-butylamido)2-butoxymethyl($\eta^5$-2-methylindenyl)silanetitanium (IV) dimethyl,
(n-butylamido)2-butoxymethyl($\eta^5$-2-methylindenyl)silanetitanium (IV) dibenzyl,
(cyclododecylamido)2-butoxymethyl($\eta^5$-2-methylindenyl)-silanetitanium (II) 1,4-diphenyl-1,3-butadiene,
(cyclododecylamido)2-butoxymethyl($\eta^5$-2-methylindenyl)silanetitanium (II) 1,3-pentadiene,
(cyclododecylamido)2-butoxymethyl($\eta^5$-2-methylindenyl)-silanetitanium (III) 2-(N,N-dimethylamino)benzyl,
(cyclododecylamido)2-butoxymethyl($\eta^5$-2-methylindenyl) silanetitanium (IV) dimethyl,
(cyclododecylamido)2-butoxymethyl($\eta^5$-2-methylindenyl) silanetitanium (IV) dibenzyl,
(2,4,6-trimethylanilido)2-butoxymethyl($\eta^5$-2-methylindenyl)silanetitanium (II) 1,4-diphenyl-1,3-butadiene,
(2,4,6-trimethylanilido)2-butoxymethyl($\eta^5$-2-methylindenyl)silanetitanium (II) 1,3-pentadiene,
(2,4,6-trimethylanilido)2-butoxymethyl($\eta^5$-2-methylindenyl)silanetitanium (III) 2-(N,N-dimethylamino)benzyl,
(2,4,6-trimethylanilido)2-butoxymethyl($\eta^5$-2-methylindenyl)silanetitanium (IV) dimethyl,
(2,4,6-trimethylanilido)2-butoxymethyl($\eta^5$-2-methylindenyl)silanetitanium (IV) dibenzyl,
(1-adamantylamido)2-butoxymethyl($\eta^5$-2-methylindenyl)-silanetitanium (II) 1,4-diphenyl-1,3-butadiene,
(1-adamantylamido)2-butoxymethyl($\eta^5$-2-methylindenyl)silanetitanium (II) 1,3-pentadiene,
(1-adamantylamido)2-butoxymethyl($\eta^5$-2-methylindenyl)-silanetitanium (III) 2-(N,N-dimethylamino)benzyl,
(1-adamantylamido)2-butoxymethyl($\eta^5$-2-methylindenyl) silanetitanium (IV) dimethyl,
(1-adamantylamido)2-butoxymethyl($\eta^5$-2-methylindenyl) silanetitanium (IV) dibenzyl,
(n-butylamido)2-butoxymethyl($\eta^5$-3-methylindenyl) silanetitanium (II) 1,4-diphenyl-1,3-butadiene,
(n-butylamido)2-butoxymethyl($\eta^5$-3-methylindenyl) silanetitanium (II) 1,3-pentadiene,
(n-butylamido)2-butoxymethyl($\eta^5$-3-methylindenyl) silanetitanium (III) 2-(N,N-dimethylamino)benzyl,
(n-butylamido)2-butoxymethyl($\eta^5$-3-methylindenyl) silanetitanium (IV) dimethyl,
(n-butylamido)2-butoxymethyl($\eta^5$-3-methylindenyl) silanetitanium (IV) dibenzyl,
(cyclododecylamido)2-butoxymethyl($\eta^5$-3-methylindenyl)-silanetitanium (II) 1,4-diphenyl-1,3-butadiene,
(cyclododecylamido)2-butoxymethyl($\eta^5$-3-methylindenyl) silanetitanium (II) 1,3-pentadiene,
(cyclododecylamido)2-butoxymethyl($\eta^5$-3-methylindenyl)-silanetitanium (III) 2-(N,N-dimethylamino)benzyl,
(cyclododecylamido)2-butoxymethyl($\eta^5$-3-methylindenyl) silanetitanium (IV) dimethyl,
(cyclododecylamido)2-butoxymethyl($\eta^5$-3-methylindenyl) silanetitanium (IV) dibenzyl,
(2,4,6-trimethylanilido)2-butoxymethyl($\eta^5$-3-methylindenyl)silanetitanium (II) 1,4-diphenyl-1,3-butadiene,
(2,4,6-trimethylanilido)2-butoxymethyl($\eta^5$-3-methylindenyl)silanetitanium (II) 1,3-pentadiene,
(2,4,6-trimethylanilido)2-butoxymethyl($\eta^5$-3-methylindenyl)silanetitanium (III) 2-(N,N-dimethylamino)benzyl,
(2,4,6-trimethylanilido)2-butoxymethyl($\eta^5$-3-methylindenyl)silanetitanium (IV) dimethyl,
(2,4,6-trimethylanilido)2-butoxymethyl($\eta^5$-3-methylindenyl)silanetitanium (IV) dibenzyl,
(1-adamantylamido)2-butoxymethyl($\eta^5$-3-methylindenyl)-silanetitanium (II) 1,4-diphenyl-1,3-butadiene,
(1-adamantylamido)2-butoxymethyl($\eta^5$-3-methylindenyl) silanetitanium (II) 1,3-pentadiene,
(1-adamantylamido)2-butoxymethyl($\eta^5$-3-methylindenyl)-silanetitanium (III) 2-(N,N-dimethylamino)benzyl,
(1-adamantylamido)2-butoxymethyl($\eta^5$-3-methylindenyl) silanetitanium (IV) dimethyl,
(1-adamantylamido)2-butoxymethyl($\eta^5$-3-methylindenyl) silanetitanium (IV) dibenzyl,
(n-butylamido)2-butoxymethyl($\eta^5$-2,3-dimethylindenyl)-silanetitanium (II) 1,4-diphenyl-1,3-butadiene,
(n-butylamido)2-butoxymethyl($\eta^5$-2,3-dimethylindenyl) silanetitanium (II) 1,3-pentadiene,
(n-butylamido)2-butoxymethyl($\eta^5$-2,3-dimethylindenyl)-silanetitanium (III) 2-(N,N-dimethylamino)benzyl,
(n-butylamido)2-butoxymethyl($\eta^5$-2,3-dimethylindenyl) silanetitanium (IV) dimethyl,
(n-butylamido)2-butoxymethyl($\eta^5$-2,3-dimethylindenyl) silanetitanium (IV) dibenzyl,
(cyclododecylamido)2-butoxymethyl($\eta^5$-2,3-dimethylindenyl)silanetitanium (II) 1,4-diphenyl-1,3-butadiene,
(cyclododecylamido)2-butoxymethyl($\eta^5$-2,3-dimethylindenyl)silanetitanium (II) 1,3-pentadiene,
(cyclododecylamido)2-butoxymethyl($\eta^5$-2,3-dimethylindenyl)silanetitanium (III) 2-(N,N-dimethylamino)benzyl,
(cyclododecylamido)2-butoxymethyl($\eta^5$-2,3-dimethylindenyl)silanetitanium (IV) dimethyl,
(cyclododecylamido)2-butoxymethyl($\eta^5$-2,3-dimethylindenyl)silanetitanium (IV) dibenzyl,
(2,4,6-trimethylanilido)2-butoxymethyl($\eta^5$-2,3-dimethylindenyl)silanetitanium (II) 1,4-diphenyl-1,3-butadiene,
(2,4,6-trimethylanilido)2-butoxymethyl($\eta^5$-2,3-dimethylindenyl)silanetitanium (II) 1,3-pentadiene, (2,4,6-trimethylanilido)2-butoxymethyl($\eta^5$-2,3-dimethylindenyl)silanetitanium (III) 2-(N,N-dimethylamino)benzyl, (2,4,6-trimethylanilido)2-butoxymethyl($\eta^5$-2,3-dimethylindenyl)silanetitanium (IV) dimethyl, (2,4,6-trimethylanilido)2-butoxymethyl($\eta^5$-2,3-dimethylindenyl)silanetitanium (IV) dibenzyl, (1-adamantylamido)2-butoxymethyl($\eta^5$-2,3-dimethylindenyl)silanetitanium (II) 1,4-diphenyl-1,3-butadiene, (1-adamantylamido)2-butoxymethyl($\eta^5$-2,3-dimethylindenyl)silanetitanium (II) 1,3-pentadiene, (1-adamantylamido)2-butoxymethyl($\eta^5$-2,3-dimethylindenyl)silanetitanium (III) 2-(N,N-dimethylamino)benzyl, (1-adamantylamido)2-butoxymethyl($\eta^5$-2,3-dimethylindenyl)silanetitanium (IV) dimethyl, (1-adamantylamido)2-butoxymethyl($\eta^5$-2,3-dimethylindenyl)silanetitanium (IV) dibenzyl, (n-butylamido)2-butoxymethyl($\eta^5$-2-methyl-4-phenylindenyl)silanetitanium (II) 1,4-diphenyl-1,3-butadiene, (n-butylamido)2-butoxymethyl($\eta^5$-2-methyl-4-phenylindenyl)silanetitanium (II) 1,3-pentadiene, (n-butylamido)2-butoxymethyl($\eta^5$-2-methyl-4-phenylindenyl)silanetitanium (III) 2-(N,N-dimethylamino)benzyl, (n-butylamido)2-butoxymethyl($\eta^5$-2-methyl-4-phenylindenyl)silanetitanium (IV) dimethyl, (n-butylamido)2-butoxymethyl($\eta^5$-2-methyl-4-phenylindenyl)silanetitanium (IV) dibenzyl, (cyclododecylamido)2-butoxymethyl($\eta^5$-2-methyl-4-phenylindenyl)silanetitanium (II) 1,4-diphenyl-1,3-butadiene, (cyclododecylamido)2-butoxymethyl($\eta^5$-2-methyl-4-phenylindenyl)silanetitanium (II) 1,3-pentadiene, (cyclododecylamido)2-butoxymethyl($\eta^5$-2-methyl-4-phenylindenyl)silanetitanium (III) 2-(N,N-dimethylamino)benzyl, (cyclododecylamido)2-butoxymethyl($\eta^5$-2-methyl-4-phenylindenyl)silanetitanium (IV) dimethyl, (cyclododecylamido)2-butoxymethyl($\eta^5$-2-methyl-4-phenylindenyl)silanetitanium (IV) dibenzyl, (2,4,6-trimethylanilido)2-butoxymethyl($\eta^5$-2-methyl-4-phenylindenyl)silanetitanium (II) 1,4-diphenyl-1,3-butadiene, (2,4,6-trimethylanilido)2-butoxymethyl($\eta^5$-2-methyl-4-phenylindenyl)silanetitanium (II) 1,3-pentadiene, (2,4,6-trimethylanilido)2-butoxymethyl($\eta^5$-2-methyl-4-phenylindenyl)silanetitanium (III) 2-(N,N-dimethylamino)benzyl, (2,4,6-trimethylanilido)2-butoxymethyl($\eta^5$-2-methyl-4-phenylindenyl)silanetitanium (IV) dimethyl, (2,4,6-trimethylanilido)2-butoxymethyl($\eta^5$-2-methyl-4-phenylindenyl)silanetitanium (IV) dibenzyl, (1-adamantylamido)2-butoxymethyl($\eta^5$-2-methyl-4-phenylindenyl)silanetitanium (II) 1,4-diphenyl-1,3-butadiene, (1-adamantylamido)2-butoxymethyl($\eta^5$-2-methyl-4-phenylindenyl)silanetitanium (II) 1,3-pentadiene, (1-adamantylamido)2-butoxymethyl($\eta^5$-2-methyl-4-phenylindenyl)silanetitanium (III) 2-(N,N-dimethylamino)benzyl, (1-adamantylamido)2-butoxymethyl($\eta^5$-2-methyl-4-phenylindenyl)silanetitanium (IV) dimethyl, (1-adamantylamido)2-butoxymethyl($\eta^5$-2-methyl-4-phenylindenyl)silanetitanium (IV) dibenzyl, (n-butylamido)2-butoxymethyl($\eta^5$-tetrahydrofluorenyl)silanetitanium (II) 1,4-diphenyl-1,3-butadiene, (n-butylamido)2-butoxymethyl($\eta^5$-tetrahydrofluorenyl)silanetitanium (II) 1,3-pentadiene, (n-butylamido)2-butoxymethyl($\eta^5$-tetrahydrofluorenyl)silanetitanium (III) 2-(N,N-dimethylamino)benzyl, (n-butylamido)2-butoxymethyl($\eta^5$-tetrahydrofluorenyl)silanetitanium (IV) dimethyl, (n-butylamido)2-butoxymethyl($\eta^5$-tetrahydrofluorenyl)silanetitanium (IV) dibenzyl, (cyclododecylamido)2-butoxymethyl($\eta^5$-tetrahydrofluorenyl)silanetitanium (II) 1,4-diphenyl-1,3-butadiene, (cyclododecylamido)2-butoxymethyl($\eta^5$-tetrahydrofluorenyl)silanetitanium (II) 1,3-pentadiene, (cyclododecylamido)2-butoxymethyl($\eta^5$-tetrahydrofluorenyl)silanetitanium (III) 2-(N,N-dimethylamino)benzyl, (cyclododecylamido)2-butoxymethyl($\eta^5$-tetrahydrofluorenyl)silanetitanium (IV) dimethyl, (cyclododecylamido)2-butoxymethyl($\eta^5$-tetrahydrofluorenyl)silanetitanium (IV) dibenzyl, (2,4,6-trimethylanilido)2-butoxymethyl($\eta^5$-tetrahydrofluorenyl)silanetitanium (II) 1,4-diphenyl-1,3-butadiene, (2,4,6-trimethylanilido)2-butoxymethyl($\eta^5$-tetrahydrofluorenyl)silanetitanium (II) 1,3-pentadiene, (2,4,6-trimethylanilido)2-butoxymethyl($\eta^5$-tetrahydrofluorenyl)silanetitanium (III) 2-(N,N-dimethylamino)benzyl, (2,4,6-trimethylanilido)2-butoxymethyl($\eta^5$-tetrahydrofluorenyl)silanetitanium (IV) dimethyl, (2,4,6-trimethylanilido)2-butoxymethyl($\eta^5$-tetrahydrofluorenyl)silanetitanium (IV) dibenzyl, (1-adamantylamido)2-butoxymethyl($\eta^5$-tetrahydrofluorenyl)silanetitanium (II) 1,4-diphenyl-1,3-butadiene, (1-adamantylamido)2-butoxymethyl($\eta^5$-tetrahydrofluorenyl)silanetitanium (II) 1,3-pentadiene, (1-adamantylamido)2-butoxymethyl($\eta^5$-tetrahydrofluorenyl)silanetitanium (III) 2-(N,N-dimethylamino)benzyl, (1-adamantylamido)2-butoxymethyl($\eta^5$-tetrahydrofluorenyl)silanetitanium (IV) dimethyl, (1-adamantylamido)2-butoxymethyl($\eta^5$-tetrahydrofluorenyl)silanetitanium (IV) dibenzyl, ethoxymethylsilanediyl complexes (n-butylamido)ethoxymethyl($\eta^5$-tetramethylcyclopentadienyl)silanetitanium (II) 1,4-diphenyl-1,3-butadiene, (n-butylamido)ethoxymethyl($\eta^5$-tetramethylcyclopentadienyl)silanetitanium (II) 1,3-pentadiene, (n-butylamido)ethoxymethyl($\eta^5$-tetramethylcyclopentadienyl)silanetitanium (III) 2-(N,N-dimethylamino)benzyl, (n-butylamido)ethoxymethyl($\eta^5$-tetramethylcyclopentadienyl)silanetitanium (IV) dimethyl, (n-butylamido)ethoxymethyl($\eta^5$-tetramethylcyclopentadienyl)silanetitanium (IV) dibenzyl, (cyclododecylamido)ethoxymethyl($\eta^5$-tetramethylcyclopentadienyl)silanetitanium (II) 1,4-diphenyl-1,3-butadiene, (cyclododecylamido)ethoxymethyl($\eta^5$-tetramethylcyclopentadienyl)silanetitanium (II) 1,3-pentadiene, (cyclododecylamido)ethoxymethyl($\eta^5$-tetramethylcyclopentadienyl)silanetitanium (III) 2-(N,N-dimethylamino)benzyl,
(cyclododecylamido)ethoxymethyl($\eta^5$-tetramethylcyclopentadienyl)silanetitanium (IV) dimethyl,
(cyclododecylamido)ethoxymethyl($\eta^5$-tetramethylcyclopentadienyl)silanetitanium (IV) dibenzyl,
(2,4,6-trimethylanilido)ethoxymethyl($\eta^5$-tetramethylcyclopentadienyl)silanetitanium (II) 1,4-diphenyl-1,3-butadiene,
(2,4,6-trimethylanilido)ethoxymethyl($\eta^5$-tetramethylcyclopentadienyl)silanetitanium (II) 1,3-pentadiene,
(2,4,6-trimethylanilido)ethoxymethyl($\eta^5$-tetramethylcyclopentadienyl)silanetitanium (III) 2-(N,N-dimethylamino)benzyl,
(2,4,6-trimethylanilido)ethoxymethyl($\eta^5$-tetramethylcyclopentadienyl)silanetitanium (IV) dimethyl,
(2,4,6-trimethylanilido)ethoxymethyl($\eta^5$-tetramethylcyclopentadienyl)silanetitanium (IV) dibenzyl,
(1-adamantylamido)ethoxymethyl($\eta^5$-tetramethylcyclopentadienyl)silanetitanium (II) 1,4-diphenyl-1,3-butadiene,
(1-adamantylamido)ethoxymethyl($\eta^5$-tetramethylcyclopentadienyl)silanetitanium (II) 1,3-pentadiene,
(1-adamantylamido)ethoxymethyl($\eta^5$-tetramethylcyclopentadienyl)silanetitanium (III) 2-(N,N-dimethylamino)benzyl,
(1-adamantylamido)ethoxymethyl($\eta^5$-tetramethylcyclopentadienyl)silanetitanium (IV) dimethyl,
(1-adamantylamido)ethoxymethyl($\eta^5$-tetramethylcyclopentadienyl)silanetitanium (IV) dibenzyl,
(n-butylamido)ethoxymethyl($\eta^5$-2-methylindenyl) silanetitanium (II) 1,4-diphenyl-1,3-butadiene,
(n-butylamido)ethoxymethyl($\eta^5$-2-methylindenyl) silanetitanium (II) 1,3-pentadiene,
(n-butylamido)ethoxymethyl($\eta^5$-2-methylindenyl) silanetitanium (III) 2-(N,N-dimethylamino)benzyl,
(n-butylamido)ethoxymethyl($\eta^5$-2-methylindenyl) silanetitanium (IV) dimethyl,
(n-butylamido)ethoxymethyl($\eta^5$-2-methylindenyl) silanetitanium (IV) dibenzyl,
(cyclododecylamido)ethoxymethyl($\eta^5$-2-methylindenyl)-silanetitanium (II) 1,4-diphenyl-1,3-butadiene,
(cyclododecylamido)ethoxymethyl($\eta^5$-2-methylindenyl) silanetitanium (II) 1,3-pentadiene,
(cyclododecylamido)ethoxymethyl($\eta^5$-2-methylindenyl) silanetitanium (III) 2-(N,N-dimethylamino)benzyl,
(cyclododecylamido)ethoxymethyl($\eta^5$-2-methylindenyl) silanetitanium (IV) dimethyl,
(cyclododecylamido)ethoxymethyl($\eta^5$-2-methylindenyl) silanetitanium (IV) dibenzyl,
(2,4,6-trimethylanilido)ethoxymethyl($\eta^5$-2-methylindenyl) silanetitanium (II) 1,4-diphenyl-1,3-butadiene,
(2,4,6-trimethylanilido)ethoxymethyl($\eta^5$-2-methylindenyl) silanetitanium (II) 1,3-pentadiene,
(2,4,6-trimethylanilido)ethoxymethyl($\eta^5$-2-methylindenyl) silanetitanium (III) 2-(N,N-dimethylamino)benzyl,
(2,4,6-trimethylanilido)ethoxymethyl($\eta^5$-2-methylindenyl) silanetitanium (IV) dimethyl,
(2,4,6-trimethylanilido)ethoxymethyl($\eta^5$-2-methylindenyl) silanetitanium (IV) dibenzyl,
(1-adamantylamido)ethoxymethyl($\eta^5$-2-methylindenyl)-silanetitanium (II) 1,4-diphenyl-1,3-butadiene,
(1-adamantylamido)ethoxymethyl($\eta^5$-2-methylindenyl)-silanetitanium (II) 1,3-pentadiene,
(1-adamantylamido)ethoxymethyl($\eta^5$-2-methylindenyl)-silanetitanium (III) 2-(N,N-dimethylamino)benzyl,
(1-adamantylamido)ethoxymethyl($\eta^5$-2-methylindenyl) silanetitanium (IV) dimethyl,
(1-adamantylamido)ethoxymethyl($\eta^5$-2-methylindenyl) silanetitanium (IV) dibenzyl,
(n-butylamido)ethoxymethyl($\eta^5$-3-methylindenyl) silanetitanium (II) 1,4-diphenyl-1,3-butadiene,
(n-butylamido)ethoxymethyl($\eta^5$-3-methylindenyl) silanetitanium (II) 1,3-pentadiene,
(n-butylamido)ethoxymethyl($\eta^5$-3-methylindenyl) silanetitanium (III) 2-(N,N-dimethylamino)benzyl,
(n-butylamido)ethoxymethyl($\eta^5$-3-methylindenyl) silanetitanium (IV) dimethyl,
(n-butylamido)ethoxymethyl($\eta^5$-3-methylindenyl) silanetitanium (IV) dibenzyl,
(cyclododecylamido)ethoxymethyl($\eta^5$-3-methylindenyl)-silanetitanium (II) 1,4-diphenyl-1,3-butadiene,
(cyclododecylamido)ethoxymethyl($\eta^5$-3-methylindenyl) silanetitanium (II) 1,3-pentadiene,
(cyclododecylamido)ethoxymethyl($\eta^5$-3-methylindenyl)-silanetitanium (III) 2-(N,N-dimethylamino)benzyl,
(cyclododecylamido)ethoxymethyl($\eta^5$-3-methylindenyl) silanetitanium (IV) dimethyl,
(cyclododecylamido)ethoxymethyl($\eta^5$-3-methylindenyl) silanetitanium (IV) dibenzyl,
(2,4,6-trimethylanilido)ethoxymethyl($\eta^5$-3-methylindenyl) silanetitanium (II) 1,4-diphenyl-1,3-butadiene,
(2,4,6-trimethylanilido)ethoxymethyl($\eta^5$-3-methylindenyl) silanetitanium (II) 1,3-pentadiene,
(2,4,6-trimethylanilido)ethoxymethyl($\eta^5$-3-methylindenyl) silanetitanium (III) 2-(N,N-dimethylamino)benzyl,
(2,4,6-trimethylanilido)ethoxymethyl($\eta^5$-3-methylindenyl) silanetitanium (IV) dimethyl,
2,4,6-trimethylanilido)ethoxymethyl($\eta^5$-3-methylindenyl) silanetitanium (IV) dibenzyl,
(1-adamantylamido)ethoxymethyl($\eta^5$-3-methylindenyl)-silanetitanium (II) 1,4-diphenyl-1,3-butadiene,
(1-adamantylamido)ethoxymethyl($\eta^5$-3-methylindenyl)-silanetitanium (II) 1,3-pentadiene,
(1-adamantylamido)ethoxymethyl($\eta^5$-3-methylindenyl)-silanetitanium (III) 2-(N,N-dimethylamino)benzyl,
(1-adamantylamido)ethoxymethyl($\eta^5$-3-methylindenyl) silanetitanium (IV) dimethyl,
(1-adamantylamido)ethoxymethyl($\eta^5$-3-methylindenyl) silanetitanium (IV) dibenzyl,
(n-butylamido)ethoxymethyl($\eta^5$-2,3-dimethylindenyl)-silanetitanium (II) 1,4-diphenyl-1,3-butadiene,
(n-butylamido)ethoxymethyl($\eta^5$-2,3-dimethylindenyl) silanetitanium (II) 1,3-pentadiene,
(n-butylamido)ethoxymethyl($\eta^5$-2,3-dimethylindenyl)-silanetitanium (III) 2-(N,N-dimethylamino)benzyl,
(n-butylamido)ethoxymethyl($\eta^5$-2,3-dimethylindenyl) silanetitanium (IV) dimethyl,
(n-butylamido)ethoxymethyl($\eta^5$-2,3-dimethylindenyl) silanetitanium (IV) dibenzyl,
(cyclododecylamido)ethoxymethyl($\eta^5$-2,3-dimethylindenyl)-silanetitanium (II) 1,4-diphenyl-1,3-butadiene,
(cyclododecylamido)ethoxymethyl($\eta^5$-2,3-dimethylindenyl)silanetitanium (II) 1,3-pentadiene, (cyclododecylamido)ethoxymethyl($\eta^5$-2,3-dimethylindenyl)-silanetitanium (III) 2-(N,N-dimethylamino)benzyl,
(cyclododecylamido)ethoxymethyl($\eta^5$-2,3-dimethylindenyl)silanetitanium (IV) dimethyl,
(cyclododecylamido)ethoxymethyl($\eta^5$-2,3-dimethylindenyl)silanetitanium (IV) dibenzyl,
2,4,6-trimethylanilido)ethoxymethyl($\eta^5$-2,3-dimethylindenyl)silanetitanium (II) 1,4-diphenyl-1,3-butadiene,
2,4,6-trimethylanilido)ethoxymethyl($\eta^5$-2,3-dimethylindenyl)silanetitanium (II) 1,3-pentadiene,
2,4,6-trimethylanilido)ethoxymethyl($\eta^5$-2,3-dimethylindenyl)silanetitanium (III) 2-(N,N-dimethylamino)benzyl,
2,4,6-trimethylanilido)ethoxymethyl($\eta^5$-2,3-dimethylindenyl)silanetitanium (IV) dimethyl,
2,4,6-trimethylanilido)ethoxymethyl($\eta^5$-2,3-dimethylindenyl)silanetitanium (IV) dibenzyl,
(1-adamantylamido)ethoxymethyl($\eta^5$-2,3-dimethylindenyl)-silanetitanium (II) 1,4-diphenyl-1,3-butadiene,
(1-adamantylamido)ethoxymethyl($\eta^5$-2,3-dimethylindenyl)silanetitanium (II) 1,3-pentadiene,
(1-adamantylamido)ethoxymethyl($\eta^5$-2,3-dimethylindenyl)-silanetitanium (III) 2-(N,N-dimethylamino)benzyl,
(1-adamantylamido)ethoxymethyl($\eta^5$-2,3-dimethylindenyl)silanetitanium (IV) dimethyl,
(1-adamantylamido)ethoxymethyl($\eta^5$-2,3-dimethylindenyl)silanetitanium (IV) dibenzyl,
(n-butylamido)ethoxymethyl($\eta^5$-2-methyl-4-phenylindenyl)-silanetitanium (II) 1,4-diphenyl-1,3-butadiene,
(n-butylamido)ethoxymethyl($\eta^5$-2-methyl-4-phenylindenyl)silanetitanium (II) 1,3-pentadiene,
(n-butylamido)ethoxymethyl($\eta^5$-2-methyl-4-phenylindenyl)-silanetitanium (III) 2-(N,N-dimethylamino)benzyl,
(n-butylamido)ethoxymethyl($\eta^5$-2-methyl-4-phenylindenyl)silanetitanium (IV) dimethyl,
(n-butylamido)ethoxymethyl($\eta^5$-2-methyl-4-phenylindenyl)silanetitanium (IV) dibenzyl,
(cyclododecylamido)ethoxymethyl($\eta^5$-2-methyl-4-phenylindenyl)silanetitanium (II) 1,4-diphenyl-1,3-butadiene,
(cyclododecylamido)ethoxymethyl($\eta^5$-2-methyl-4-phenylindenyl)silanetitanium (II) 1,3-pentadiene,
(cyclododecylamido)ethoxymethyl($\eta^5$-2-methyl-4-phenylindenyl)silanetitanium (III) 2-(N,N-dimethylamino)benzyl,
(cyclododecylamido)ethoxymethyl($\eta^5$-2-methyl-4-phenylindenyl)silanetitanium (IV) dimethyl,
(cyclododecylamido)ethoxymethyl($\eta^5$-2-methyl-4-phenylindenyl)silanetitanium (IV) dibenzyl,
(2,4,6-trimethylanilido)ethoxymethyl($\eta^5$-2-methyl-4-phenylindenyl)silanetitanium (II) 1,4-diphenyl-1,3-butadiene,
(2,4,6-trimethylanilido)ethoxymethyl($\eta^5$-2-methyl-4-phenylindenyl)silanetitanium (II) 1,3-pentadiene,
(2,4,6-trimethylanilido)ethoxymethyl($\eta^5$-2-methyl-4-phenylindenyl)silanetitanium (III) 2-(N,N-dimethylamino)benzyl,
(2,4,6-trimethylanilido)ethoxymethyl($\eta^5$-2-methyl-4-phenylindenyl)silanetitanium (IV) dimethyl,
(2,4,6-trimethylanilido)ethoxymethyl($\eta^5$-2-methyl-4-phenylindenyl)silanetitanium (IV) dibenzyl,
(1-adamantylamido)ethoxymethyl($\eta^5$-2-methyl-4-phenylindenyl)silanetitanium (II) 1,4-diphenyl-1,3-butadiene,
(1-adamantylamido)ethoxymethyl($\eta^5$-2-methyl-4-phenylindenyl)silanetitanium (II) 1,3-pentadiene,
(1-adamantylamido)ethoxymethyl($\eta^5$-2-methyl-4-phenylindenyl)silanetitanium (III) 2-(N,N-dimethylamino)benzyl,
(1-adamantylamido)ethoxymethyl($\eta^5$-2-methyl-4-phenylindenyl)silanetitanium (IV) dimethyl,
(1-adamantylamido)ethoxymethyl($\eta^5$-2-methyl-4-phenylindenyl)silanetitanium (IV) dibenzyl,
(n-butylamido)ethoxymethyl($\eta^5$-tetrahydrofluorenyl)-silanetitanium (II) 1,4-diphenyl-1,3-butadiene,
(n-butylamido)ethoxymethyl($\eta^5$-tetrahydrofluorenyl)-silanetitanium (II) 1,3-pentadiene,
(n-butylamido)ethoxymethyl($\eta^5$-tetrahydrofluorenyl)-silanetitanium (III) 2-(N,N-dimethylamino)benzyl,
(n-butylamido)ethoxymethyl($\eta^5$-tetrahydrofluorenyl)-silanetitanium (IV) dimethyl,
(n-butylamido)ethoxymethyl($\eta^5$-tetrahydrofluorenyl)-silanetitanium (IV) dibenzyl,
(cyclododecylamido)ethoxymethyl($\eta^5$-tetrahydrofluorenyl)-silanetitanium (II) 1,4-diphenyl-1,3-butadiene,
(cyclododecylamido)ethoxymethyl($\eta^5$-tetrahydrofluorenyl)-silanetitanium (II) 1,3-pentadiene,
(cyclododecylamido)ethoxymethyl($\eta^5$-tetrahydrofluorenyl)-silanetitanium (III) 2-(N,N-dimethylamino)benzyl,
(cyclododecylamido)ethoxymethyl($\eta^5$-tetrahydrofluorenyl)-silanetitanium (IV) dimethyl,
(cyclododecylamido)ethoxymethyl($\eta^5$-tetrahydrofluorenyl)-silanetitanium (IV) dibenzyl,
(2,4,6-trimethylanilido)ethoxymethyl($\eta^5$-tetrahydrofluorenyl)silanetitanium (II) 1,4-diphenyl-1,3-butadiene,
(2,4,6-trimethylanilido)ethoxymethyl($\eta^5$-tetrahydrofluorenyl)silanetitanium (II) 1,3-pentadiene,
(2,4,6-trimethylanilido)ethoxymethyl($\eta^5$-tetrahydrofluorenyl)silanetitanium (III) 2-(N,N-dimethylamino)benzyl,
(2,4,6-trimethylanilido)ethoxymethyl($\eta^5$-tetrahydrofluorenyl)silanetitanium (IV) dimethyl,
(2,4,6-trimethylanilido)ethoxymethyl($\eta^5$-tetrahydrofluorenyl)silanetitanium (IV) dibenzyl,
(1-adamantylamido)ethoxymethyl($\eta^5$-tetrahydrofluorenyl)-silanetitanium (II) 1,4-diphenyl-1,3-butadiene,
(1-adamantylamido)ethoxymethyl($\eta^5$-tetrahydrofluorenyl)-silanetitanium (II) 1,3-pentadiene,
(1-adamantylamido)ethoxymethyl($\eta^5$-tetrahydrofluorenyl)-silanetitanium (III) 2-(N,N-dimethylamino)benzyl,
(1-adamantylamido)ethoxymethyl($\eta^5$-tetrahydrofluorenyl)-silanetitanium (IV) dimethyl,
(1-adamantylamido)ethoxymethyl($\eta^5$-tetrahydrofluorenyl)-silanetitanium (IV) dibenzyl,
isopropoxymethylsilandiyl complexes
(n-butylamido)isopropoxymethyl($\eta^5$-tetramethylcyclopentadienyl)silanetitanium (II) 1,4-diphenyl-1,3-butadiene,
(n-butylamido)isopropoxymethyl($\eta^5$-tetramethylcyclopentadienyl)silanetitanium (II) 1,3-pentadiene,
(n-butylamido)isopropoxymethyl($\eta^5$-tetramethylcyclopentadienyl)silanetitanium (III) 2-(N,N-dimethylamino)benzyl,
(n-butylamido)isopropoxymethyl($\eta^5$-tetramethylcyclopentadienyl)silanetitanium (IV) dimethyl,
(n-butylamido)isopropoxymethyl($\eta^5$-tetramethylcyclopentadienyl)silanetitanium (IV) dibenzyl, (cyclododecylamido)isopropoxymethyl($\eta^5$-tetramethylcyclopentadienyl)silanetitanium (II) 1,4-diphenyl-1,3-butadiene,
(cyclododecylamido)isopropoxymethyl($\eta^5$-tetramethylcyclopentadienyl)silanetitanium (II) 1,3-pentadiene,
(cyclododecylamido)isopropoxymethyl($\eta^5$-tetramethylcyclopentadienyl)silanetitanium (III) 2-(N,N-dimethylamino)benzyl,
(cyclododecylamido)isopropoxymethyl($\eta^5$-tetramethylcyclopentadienyl)silanetitanium (IV) dimethyl,
(cyclododecylamido)isopropoxymethyl($\eta^5$-tetramethylcyclopentadienyl)silanetitanium (IV) dibenzyl,
(2,4,6-trimethylanilido)isopropoxymethyl($\eta^5$-tetramethylcyclopentadienyl)silanetitanium (II) 1,4-diphenyl-1,3-butadiene,
(2,4,6-trimethylanilido)isopropoxymethyl($\eta^5$-tetramethylcyclopentadienyl)silanetitanium (II) 1,3-pentadiene,
(2,4,6-trimethylanilido)isopropoxymethyl($\eta^5$-tetramethylcyclopentadienyl)silanetitanium (III) 2-(N,N-dimethylamino)benzyl,
(2,4,6-trimethylanilido)isopropoxymethyl($\eta^5$-tetramethylcyclopentadienyl)silanetitanium (IV) dimethyl,
(2,4,6-trimethylanilido)isopropoxymethyl($\eta^5$-tetramethylcyclopentadienyl)silanetitanium (IV) dibenzyl,
(1-adamantylamido)isopropoxymethyl($\eta^5$-tetramethylcyclopentadienyl)silanetitanium (II) 1,4-diphenyl-1,3-butadiene,
(1-adamantylamido)isopropoxymethyl($\eta^5$-tetramethylcyclopentadienyl)silanetitanium (II) 1,3-pentadiene,
(1-adamantylamido)isopropoxymethyl($\eta^5$-tetramethylcyclopentadienyl)silanetitanium (III) 2-(N,N-dimethylamino)benzyl,
(1-adamantylamido)isopropoxymethyl($\eta^5$-tetramethylcyclopentadienyl)silanetitanium (IV) dimethyl,
(1-adamantylamido)isopropoxymethyl($\eta^5$-tetramethylcyclopentadienyl)silanetitanium (IV) dibenzyl,
(n-butylamido)isopropoxymethyl($\eta^5$-2-methylindenyl)silanetitanium (II) 1,4-diphenyl-1,3-butadiene,
(n-butylamido)isopropoxymethyl($\eta^5$-2-methylindenyl)silanetitanium (II) 1,3-pentadiene,
(n-butylamido)isopropoxymethyl($\eta^5$-2-methylindenyl)silanetitanium (III) 2-(N,N-dimethylamino)benzyl,
(n-butylamido)isopropoxymethyl($\eta^5$-2-methylindenyl)silanetitanium (IV) dimethyl,
(n-butylamido)isopropoxymethyl($\eta^5$-2-methylindenyl)silanetitanium (IV) dibenzyl,
(cyclododecylamido)isopropoxymethyl($\eta^5$-2-methylindenyl)-silanetitanium (II) 1,4-diphenyl-1,3-butadiene,
(cyclododecylamido)isopropoxymethyl($\eta^5$-2-methylindenyl)silanetitanium (II) 1,3-pentadiene,
(cyclododecylamido)isopropoxymethyl($\eta^5$-2-methylindenyl)-silanetitanium (III) 2-(N,N-dimethylamino)benzyl,
(cyclododecylamido)isopropoxymethyl($\eta^5$-2-methylindenyl)silanetitanium (IV) dimethyl,
(cyclododecylamido)isopropoxymethyl($\eta^5$-2-methylindenyl)silanetitanium (IV) dibenzyl,
(2,4,6-trimethylanilido)isopropoxymethyl($\eta^5$-2-methylindenyl)silanetitanium (II) 1,4-diphenyl-1,3-butadiene,
(2,4,6-trimethylanilido)isopropoxymethyl($\eta^5$-2-methylindenyl)silanetitanium (II) 1,3-pentadiene,
(2,4,6-trimethylanilido)isopropoxymethyl($\eta^5$-2-methylindenyl)silanetitanium (III) 2-(N,N-dimethylamino)benzyl,
(2,4,6-trimethylanilido)isopropoxymethyl($\eta^5$-2-methylindenyl)silanetitanium (IV) dimethyl,
(2,4,6-trimethylanilido)isopropoxymethyl($\eta^5$-2-methylindenyl)silanetitanium (IV) dibenzyl,
(1-adamantylamido)isopropoxymethyl($\eta^5$-2-methylindenyl)-silanetitanium (II) 1,4-diphenyl-1,3-butadiene,
(1-adamantylamido)isopropoxymethyl($\eta^5$-2-methylindenyl)silanetitanium (II) 1,3-pentadiene,
(1-adamantylamido)isopropoxymethyl($\eta^5$-2-methylindenyl)-silanetitanium (III) 2-(N,N-dimethylamino)benzyl,
(1-adamantylamido)isopropoxymethyl($\eta^5$-2-methylindenyl)silanetitanium (IV) dimethyl,
(1-adamantylamido)isopropoxymethyl($\eta^5$-2-methylindenyl)silanetitanium (IV) dibenzyl,
(n-butylamido)isopropoxymethyl($\eta^5$-3-methylindenyl)silanetitanium (II) 1,4-diphenyl-1,3-butadiene,
(n-butylamido)isopropoxymethyl($\eta^5$-3-methylindenyl)silanetitanium (II) 1,3-pentadiene,
(n-butylamido)isopropoxymethyl($\eta^5$-3-methylindenyl)silanetitanium (III) 2-(N,N-dimethylamino)benzyl,
(n-butylamido)isopropoxymethyl($\eta^5$-3-methylindenyl)silanetitanium (IV) dimethyl,
(n-butylamido)isopropoxymethyl($\eta^5$-3-methylindenyl)silanetitanium (IV) dibenzyl,
(cyclododecylamido)isopropoxymethyl($\eta^5$-3-methylindenyl)-silanetitanium (II) 1,4-diphenyl-1,3-butadiene,
(cyclododecylamido)isopropoxymethyl($\eta^5$-3-methylindenyl)silanetitanium (II) 1,3-pentadiene,
(cyclododecylamido)isopropoxymethyl($\eta^5$-3-methylindenyl)-silanetitanium (III) 2-(N,N-dimethylamino)benzyl,
(cyclododecylamido)isopropoxymethyl($\eta^5$-3-methylindenyl)silanetitanium (IV) dimethyl,
(cyclododecylamido)isopropoxymethyl($\eta^5$-3-methylindenyl)silanetitanium (IV) dibenzyl,
(2,4,6-trimethylanilido)isopropoxymethyl($\eta^5$-3-methylindenyl)silanetitanium (II) 1,4-diphenyl-1,3-butadiene,
(2,4,6-trimethylanilido)isopropoxymethyl($\eta^5$-3-methylindenyl)silanetitanium (II) 1,3-pentadiene,
(2,4,6-trimethylanilido)isopropoxymethyl($\eta^5$-3-methylindenyl)silanetitanium (III) 2-(N,N-dimethylamino)benzyl,
(5 2,4,6-trimethylanilido)isopropoxymethyl($\eta^5$-3-methylindenyl)silanetitanium (IV) dimethyl,
(2,4,6-trimethylanilido)isopropoxymethyl($\eta^5$-3-methylindenyl)silanetitanium (IV) dibenzyl,
(1-adamantylamido)isopropoxymethyl($\eta^5$-3-methylindenyl)-silanetitanium (II) 1,4-diphenyl-1,3-butadiene,
(1-adamantylamido)isopropoxymethyl($\eta^5$-3-methylindenyl)silanetitanium (II) 1,3-pentadiene,
(1-adamantylamido)isopropoxymethyl($\eta^5$-3-methylindenyl)-silanetitanium (III) 2-(N,N-dimethylamino)benzyl,
(1-adamantylamido)isopropoxymethyl($\eta^5$-3-methylindenyl)silanetitanium (IV) dimethyl, (1-adamantylamido)isopropoxymethyl($\eta^5$-3-methylindenyl)silanetitanium (IV) dibenzyl,
(n-butylamido)isopropoxymethyl($\eta^5$-2,3-dimethylindenyl)silanetitanium (II) 1,4-diphenyl-1,3-butadiene,
(n-butylamido)isopropoxymethyl($\eta^5$-2,3-dimethylindenyl)silanetitanium (II) 1,3-pentadiene,
(n-butylamido)isopropoxymethyl($\eta^5$-2,3-dimethylindenyl)silanetitanium (III) 2-(N,N-dimethylamino)benzyl,
(n-butylamido)isopropoxymethyl($\eta^5$-2,3-dimethylindenyl)silanetitanium (IV) dimethyl,
(n-butylamido)isopropoxymethyl($\eta^5$-2,3-dimethylindenyl)silanetitanium (IV) dibenzyl,
(cyclododecylamido)isopropoxymethyl($\eta^5$-2,3-dimethylindenyl)silanetitanium (II) 1,4-diphenyl-1,3-butadiene,
(cyclododecylamido)isopropoxymethyl($\eta^5$-2,3-dimethylindenyl)silanetitanium (II) 1,3-pentadiene,
(cyclododecylamido)isopropoxymethyl($\eta^5$-2,3-dimethylindenyl)silanetitanium (III) 2-(N,N-dimethylamino)benzyl,
(cyclododecylamido)isopropoxymethyl($\eta^5$-2,3-dimethylindenyl)silanetitanium (IV) dimethyl,
(cyclododecylamido)isopropoxymethyl($\eta^5$-2,3-dimethylindenyl)silanetitanium (IV) dibenzyl,
(2,4,6-trimethylanilido)isopropoxymethyl($\eta^5$-2,3-dimethylindenyl)silanetitanium (II) 1,4-diphenyl-1,3-butadiene,
(2,4,6-trimethylanilido)isopropoxymethyl($\eta^5$-2,3-dimethylindenyl)silanetitanium (II) 1,3-pentadiene,
(2,4,6-trimethylanilido)isopropoxymethyl($\eta^5$-2,3-dimethylindenyl)silanetitanium (III) 2-(N,N-dimethylamino)benzyl,
(2,4,6-trimethylanilido)isopropoxymethyl($\eta^5$-2,3-dimethylindenyl)silanetitanium (IV) dimethyl,
(2,4,6-trimethylanilido)isopropoxymethyl($\eta^5$-2,3-dimethylindenyl)silanetitanium (IV) dibenzyl,
(1-adamantylamido)isopropoxymethyl($\eta^5$-2,3-dimethylindenyl)silanetitanium (II) 1,4-diphenyl-1,3-butadiene,
(1-adamantylamido)isopropoxymethyl($\eta^5$-2,3-dimethylindenyl)silanetitanium (II) 1,3-pentadiene,
(1-adamantylamido)isopropoxymethyl($\eta^5$-2,3-dimethylindenyl)silanetitanium (III) 2-(N,N-dimethylamino)benzyl,
(1-adamantylamido)isopropoxymethyl($\eta^5$-2,3-dimethylindenyl)silanetitanium (IV) dimethyl,
(1-adamantylamido)isopropoxymethyl($\eta^5$-2,3-dimethylindenyl)silanetitanium (IV) dibenzyl,
(n-butylamido)isopropoxymethyl($\eta^5$-2-methyl-4-phenylindenyl)silanetitanium (II) 1,4-diphenyl-1,3-butadiene,
(n-butylamido)isopropoxymethyl($\eta^5$-2-methyl-4-phenylindenyl)silanetitanium (II) 1,3-pentadiene,
(n-butylamido)isopropoxymethyl($\eta^5$-2-methyl-4-phenylindenyl)silanetitanium (III) 2-(N,N-dimethylamino)benzyl,
(n-butylamido)isopropoxymethyl($\eta^5$-2-methyl-4-phenylindenyl)silanetitanium (IV) dimethyl,
(n-butylamido)isopropoxymethyl($\eta^5$-2-methyl-4-phenylindenyl)silanetitanium (IV) dibenzyl,
(cyclododecylamido)isopropoxymethyl($\eta^5$-2-methyl-4-phenylindenyl)silanetitanium (II) 1,4-diphenyl-1,3-butadiene,
(cyclododecylamido)isopropoxymethyl($\eta^5$-2-methyl-4-phenylindenyl)silanetitanium (II) 1,3-pentadiene,
(cyclododecylamido)isopropoxymethyl($\eta^5$-2-methyl-4-phenylindenyl)silanetitanium (III) 2-(N,N-dimethylamino)benzyl,
(cyclododecylamido)isopropoxymethyl($\eta^5$-2-methyl-4-phenylindenyl)silanetitanium (IV) dimethyl,
(cyclododecylamido)isopropoxymethyl($\eta^5$-2-methyl-4-phenylindenyl)silanetitanium (IV) dibenzyl,
(2,4,6-trimethylanilido)isopropoxymethyl($\eta^5$-2-methyl-4-phenylindenyl)silanetitanium (II) 1,4-diphenyl-1,3-butadiene,
(2,4,6-trimethylanilido)isopropoxymethyl($\eta^5$-2-methyl-4-phenylindenyl)silanetitanium (II) 1,3-pentadiene,
(2,4,6-trimethylanilido)isopropoxymethyl($\eta^5$-2-methyl-4-phenylindenyl)silanetitanium (III) 2-(N,N-dimethylamino)benzyl,
(2,4,6-trimethylanilido)isopropoxymethyl($\eta^5$-2-methyl-4-phenylindenyl)silanetitanium (IV) dimethyl,
(2,4,6-trimethylanilido)isopropoxymethyl($\eta^5$-2-methyl-4-phenylindenyl)silanetitanium (IV) dibenzyl,
(1-adamantylamido)isopropoxymethyl($\eta^5$-2-methyl-4-phenylindenyl)silanetitanium (II) 1,4-diphenyl-1,3-butadiene,
(1-adamantylamido)isopropoxymethyl($\eta^5$-2-methyl-4-phenylindenyl)silanetitanium (II) 1,3-pentadiene,
(1-adamantylamido)isopropoxymethyl($\eta^5$-2-methyl-4-phenylindenyl)silanetitanium (III) 2-(N,N-dimethylamino)benzyl,
(1-adamantylamido)isopropoxymethyl($\eta^5$-2-methyl-4-phenylindenyl)silanetitanium (IV) dimethyl,
(1-adamantylamido)isopropoxymethyl($\eta^5$-2-methyl-4-phenylindenyl)silanetitanium (IV) dibenzyl,
(n-butylamido)isopropoxymethyl($\eta^5$-tetrahydrofluorenyl)silanetitanium (II) 1,4-diphenyl-1,3-butadiene,
(n-butylamido)isopropoxymethyl($\eta^5$-tetrahydrofluorenyl)silanetitanium (II) 1,3-pentadiene,
(n-butylamido)isopropoxymethyl($\eta^5$-tetrahydrofluorenyl)silanetitanium (III) 2-(N,N-dimethylamino)benzyl,
(n-butylamido)isopropoxymethyl($\eta^5$-tetrahydrofluorenyl)silanetitanium (IV) dimethyl,
(n-butylamido)isopropoxymethyl($\eta^5$-tetrahydrofluorenyl)silanetitanium (IV) dibenzyl,
(cyclododecylamido)isopropoxymethyl($\eta^5$-tetrahydrofluorenyl)silanetitanium (II) 1,4-diphenyl-1,3-butadiene,
(cyclododecylamido)isopropoxymethyl($\eta^5$-tetrahydrofluorenyl)silanetitanium (II) 1,3-pentadiene,
(cyclododecylamido)isopropoxymethyl($\eta^5$-tetrahydrofluorenyl)silanetitanium (III) 2-(N,N-dimethylamino)benzyl,
(cyclododecylamido)isopropoxymethyl($\eta^5$-tetrahydrofluorenyl)silanetitanium (IV) dimethyl,
(cyclododecylamido)isopropoxymethyl($\eta^5$-tetrahydrofluorenyl)silanetitanium (IV) dibenzyl,
(2,4,6-trimethylanilido)isopropoxymethyl($\eta^5$-tetrahydrofluorenyl)silanetitanium (II) 1,4-diphenyl-1,3-butadiene,
(2,4,6-trimethylanilido)isopropoxymethyl($\eta^5$-tetrahydrofluorenyl)silanetitanium (II) 1,3-pentadiene,
(2,4,6-trimethylanilido)isopropoxymethyl($\eta^5$-tetrahydrofluorenyl)silanetitanium (III) 2-(N,N-dimethylamino)benzyl,
(2,4,6-trimethylanilido)isopropoxymethyl($\eta^5$-tetrahydrofluorenyl)silanetitanium (IV) dimethyl,
(2,4,6-trimethylanilido)isopropoxymethyl($\eta^5$-tetrahydrofluorenyl)silanetitanium (IV) dibenzyl,
(1-adamantylamido)isopropoxymethyl($\eta^5$-tetrahydrofluorenyl)silanetitanium (II) 1,4-diphenyl-1,3-butadiene,
(1-adamantylamido)isopropoxymethyl($\eta^5$-tetrahydrofluorenyl)silanetitanium (II) 1,3-pentadiene, (1-adamantylamido)isopropoxymethyl($\eta^5$-tetrahydrofluorenyl)silanetitanium (III) 2-(N,N-dimethylamino)benzyl,
(1-adamantylamido)isopropoxymethyl($\eta^5$-tetrahydrofluorenyl)silanetitanium (IV) dimethyl, and
(1-adamantylamido)isopropoxymethyl($\eta^5$-tetrahydrofluorenyl)silanetitanium (IV) dibenzyl.

Other metal complexes, especially compounds containing other Group 3, 4 or Lanthanide metals will, of course, be apparent to those skilled in the art.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, such as $C_{1-30}$ hydrocarbyl substituted Group 13 compounds, especially tri(hydrocarbyl)aluminum- or tri(hydrocarbyl)boron-compounds and halogenated derivatives thereof, having from 1 to 10 carbons in each hydrocarbyl or halogenated hydrocarbyl group, especially tris(pentafluorophenyl)borane; and nonpolymeric, inert, compatible, noncoordinating, ion forming compounds (including the use of such compounds under oxidizing conditions). A suitable activating technique is bulk electrolysis (explained in more detail hereinafter). Combinations of the foregoing activating cocatalysts and techniques may also be employed if desired. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), EP-A-520,732 (equivalent to U.S. Ser. No. 07/876,268), and WO93/23412(equivalent to U.S. Ser. Nos. 07/884,966 filed May 1, 1992), the teachings of which are hereby incorporated by reference.

Suitable nonpolymeric, inert, compatible, noncoordinating, ion forming compounds useful as cocatalysts in one embodiment of the present invention comprise a cation which is a Bronsted acid capable of donating a proton, and a compatible, noncoordinating, anion, A⁻. Preferred anions are those containing a single coordination complex comprising a charge-bearing metal or metalloid core which anion is capable of balancing the charge of the active catalyst species (the metal cation) which is formed when the two components are combined. Also, said anion can be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are well known and many, particularly such compounds containing a single boron atom in the anion portion, are available commercially.

Preferably such cocatalysts may be represented by the following general formula:

$$(L^*-H)^+_d A^{d-}$$

wherein:

L* is a neutral Lewis base;

(L*—H)⁺ is a Bronsted acid;

$A^{d-}$ is a noncoordinating, compatible anion having a charge of d-and d is an integer from 1 to 3.

More preferably d is one, that is, $A^{d-}$ is A⁻.

Highly preferably, A⁻ corresponds to the formula:

$$[BQ_4]^-$$

wherein:

B is boron in the +3 formal oxidation state; and

Q independently each occurrence is selected from hydride, dialkylamido, halide, alkoxide, aryloxide, hydrocarbyl, halocarbyl, and halosubstituted-hydrocarbyl radicals, said Q having up to 20 carbons with the proviso that in not more than one occurrence is Q halide.

In a more highly preferred embodiment, Q is a fluorinated $C_{1-20}$ hydrocarbyl group, most preferably, a fluorinated aryl group, especially, pentafluorophenyl.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis-(penta-fluorophenyl) borate,
triethylammonium tetrakis-(pentafluorophenyl) borate,
tripropylammonium tetrakis(pentafluorophenyl) borate, tri(n-butyl)ammonium tetrakis(pentafluorophenyl) borate, tri(sec-butyl)ammonium tetrakis(pentafluorophenyl)borate, N,N-dimethylanilinium tetrakis(pentafluorophenyl) borate, N,N-diethylanilinium tetrakis(pentafluoro-phenyl) borate, N,N-dimethyl(2,4,6-trimethylanilinium) tetrakis-(pentafluorophenyl) borate,
trimethylammonium tetrakis(2,3,4,6-tetrafluorophenylborate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl) borate,
N,N-dimethylanilinium tetrakis(2,3,4,6-tetrafluorophenyl) borate,
N,N-diethylanilinium tetrakis(2,3,4,6-tetrafluorophenyl) borate, and
N,N-dimethyl-(2,4,6-trimethylanilinium) tetrakis-(2,3,4,6-tetrafluorophenyl) borate.

Dialkyl ammonium salts such as:
di-(i-propyl)ammonium tetrakis(pentafluorophenyl) borate, and
dicyclohexylammonium tetrakis(pentafluorophenyl) borate.

Tri-substituted phosphonium salts such as: triphenylphosphonium tetrakis(pentafluorophenyl) borate, tri(o-tolyl)phosphonium tetrakis(penta-fluorophenyl) borate, and
tri(2,6-dimethylphenyl)-phosphonium tetrakis(pentafluorophenyl) borate.

Preferred are N,N-dimethylanilinium tetrakis(pentafluorophenyl)borate and tributylammonium tetrakis(pentafluorophenyl)borate.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having charge e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion or silylium ion and a noncoordinating, compatible anion represented by the formula:

$$©^+A^-$$

wherein:

$©^+$ is a $C_{1-20}$ carbenium ion or silylium ion; and $A^-$ is as previously defined.

A preferred carbenium ion is the trityl cation, that is triphenylcarbenium. A preferred silylium ion is triphenylsilylium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

An especially preferred activating cocatalyst comprises the combination of a trialkyl aluminum compound having from 1 to 4 carbons in each alkyl group and an ammonium salt of tetrakis(pentafluorophenyl)borate, in a molar ratio from 0.1:1 to 1:0.1, optionally up to 1000 mole percent of an alkylalumoxane with respect to M, is also present.

The activating technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0° to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally, an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, $A^-$. Preferred supporting electrolytes are salts corresponding to the formula:

$$G^+A^-;$$

wherein:

$G^+$ is a cation which is nonreactive towards the starting and resulting complex, and $A^-$ is a noncoordinating, compatible anion.

Examples of cations, $G^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode.

Preferred supporting electrolytes are tetrahydrocarbylammonium salts of tetrakis(perfluoroaryl) borates having from 1 to 10 carbons in each hydrocarbyl group, especially tetra-n-butylammonium tetrakis(pentafluorophenyl) borate.

The molar ratio of catalyst/cocatalyst employed preferably ranges from 1:10,000 to 100:1, more preferably from 1:5000 to 10:1, most preferably from 1:10 to 1:2.

In general, the catalysts can be prepared by combining the two components in a suitable solvent at a temperature within the range from about −100° C. to about 300° C. The catalyst may be separately prepared prior to use by combining the respective components or prepared in situ by combination in the presence of the monomers to be polymerized. It is preferred to form the catalyst in situ due to the exceptionally high catalytic effectiveness of catalysts prepared in this manner. The catalysts' components are sensitive to both moisture and oxygen and should be handled and transferred in an inert atmosphere.

As previously mentioned the present metal complexes are highly desirable for use in preparing supported catalysts. The presence of the alkoxy functionality in the bridging group has been discovered to be particularly beneficial in allowing the complexes to chemically bind to hydroxyl, silane or chlorosilane functionality of the substrate materials. Especially suited substrates include alumina or silica. Suitable supported catalyst systems are readily prepared by contacting the present metal complexes with the substrate optionally while subjecting to heating and/or reduced pressures. A Lewis base, especially a trialkylamine can be present to assist in the reaction between the support and the siloxane functionality of the metal complexes.

Preferred supports for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W. R. Grace & Co.) under the designations SD 3216.30, Davison Syloid 245, Davison 948 and Davison 952, and from Degussa AG under the designation Aerosil 812; and aluminas available from Akzo Chemicals Inc. under the designation Ketzen Grade B.

Supports suitable for the present invention preferably have a surface area as determined by nitrogen porosimetry using the B.E.T. method from 10 to about 1000 m$^2$/g, and preferably from about 100 to 600 m$^2$/g. The pore volume of the support, as determined by nitrogen adsorption, advantageously is between 0.1 and 3 cm$^3$/g, preferably from about 0.2 to 2 cm$^3$/g. The average particle size is not critical, but typically is from 0.5 to 500 μm, preferably from 1 to 100 μm.

Both silica and alumina are known to inherently possess small quantities of hydroxyl functionality attached to the crystal structure. When used as a support herein, these materials are preferably subjected to a heat treatment and/or chemical treatment to reduce the hydroxyl content thereof. Typical heat treatments are carried out at a temperature from 30° to 1000° C. for a duration of 10 minutes to 50 hours in an inert atmosphere or under reduced pressure. Typical chemical treatments include contacting with Lewis acid alkylating agents such as trihydrocarbyl aluminum compounds, trihydrocarbylchlorosilane compounds, trihydrocarbylalkoxysilane compounds or similar agents. Preferred silica or alumina materials for use herein have a surface hydroxyl content that is less than 0.8 mmol hydroxyl groups per gram of solid support, more preferably less than 0.5 mmol per gram. The hydroxyl content may be determined by adding an excess of dialkyl magnesium to a slurry of the solid support and determining the amount of dialkyl magnesium remaining in solution via known techniques. This method is based on the reaction:

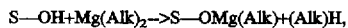

wherein S is the solid support, and Alk is a C$_{1-4}$ alkyl group.

The support may be unfunctionalized (excepting for hydroxyl groups as previously disclosed) or functionalized by treating with a silane or chlorosilane functionalizing agent to attach thereto pendant silane —(Si—R)=, or chlorosilane —(Si—Cl)= functionality, wherein R is a C$_{1-10}$ hydrocarbyl group. Suitable functionalizing agents are compounds that react with surface hydroxyl groups of the support or react with the silicon or aluminum of the matrix. Examples of suitable functionalizing agents include phenylsilane, diphenylsilane, methylphenylsilane, dimethylsilane, diethylsilane, dichlorosilane and dichlorodimethylsilane. Techniques for forming such functionalized silica or alumina compounds were previously disclosed in U.S. Pat. Nos. 3,687,920 and 3,879,368, the teachings of which are herein incorporated by reference.

The support may also be treated with an aluminum component selected from an alumoxane or an aluminum compound of the formula AlR$^1_{x'}$R$^2_{y'}$, wherein R$^1$ independently each occurrence is hydride or R, R$^2$ is hydride, R or OR, x' is 2 or 3, y' is 0 or 1 and the sum of x' and y' is 3. Examples of suitable R$^1$ and R$^2$ groups include methyl, methoxy, ethyl, ethoxy, propyl (all isomers), propoxy (all isomers), butyl (all isomers), butoxy (all isomers), phenyl, phenoxy, benzyl, and benzyloxy. Preferably, the aluminum component is selected from the group consisting of aluminoxanes and tri(C$_{1-4}$ hydrocarbyl)aluminum compounds. Most preferred aluminum components are aluminoxanes, trimethyl aluminum, triethyl aluminum, tri-isobutyl aluminum, and mixtures thereof.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O)$_{m'}$, for a cyclic alumoxane, and R$_2$Al—O(—Al(R)—O)$_{m'}$—AlR$_2$, for a linear compound, wherein R is as previously defined, and m' is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as for example trimethyl aluminum and tri-isobutyl aluminum, with water yields so-called modified or mixed alumoxanes. Preferred alumoxanes are methylalumoxane and methylalumoxane modified with minor amounts of C$_{2-4}$ alkyl groups, especially isobutyl. Alumoxanes generally contain minor to substantial amounts of starting aluminum alkyl compound.

Particular techniques for the preparation of alumoxane type compounds by contacting an aluminum alkyl compound with an inorganic salt containing water of crystallization are disclosed in U.S. Pat. No. 4,542,119. In a particular preferred embodiment an aluminum alkyl compound is contacted with a regeneratable water-containing substance such as hydrated alumina, silica or other substance. This is disclosed in EP-A-338,044. Thus the alumoxane may be incorporated into the support by reaction of a hydrated alumina or silica material, which has optionally been functionalized with silane, siloxane, hydrocarbyloxysilane, or chlorosilane groups, with a tri(C$_{1-10}$ alkyl) aluminum compound according to known techniques. For the teachings contained therein the foregoing patents and publications, or there corresponding equivalent United States applications, are hereby incorporated by reference.

The treatment of the support material in order to also include optional alumoxane or trialkylaluminum loadings involves contacting the same before, after or simultaneously with addition of the complex or activated catalyst hereunder with the alumoxane or trialkylaluminum compound, especially triethylaluminum or triisobutylaluminum. Optionally the mixture can also be heated under an inert atmosphere for a period and at a temperature sufficient to fix the alumoxane, trialkylaluminum compound, complex or catalyst system to the support. Optionally, the treated support component containing alumoxane or the trialkylaluminum compound may be subjected to one or more wash steps to remove alumoxane or trialkylaluminum not fixed to the support.

Besides contacting the support with alumoxane the alumoxane may be generated in situ by contacting an unhydrolyzed silica or alumina or a moistened silica or alumina with a trialkyl aluminum compound optionally in the presence of an inert diluent. Such a process is well known in the art, having been disclosed in EP-A-250,600, U.S. Pat. No.

4,912,075, and U.S. Pat. No. 5,008,228, the teachings of which, or of the corresponding U.S. application, are hereby incorporated by reference. Suitable aliphatic hydrocarbon diluents include pentane, isopentane, hexane, heptane, octane, isooctane, nonane, isononane, decane, cyclohexane, methylcyclohexane and combinations of two or more of such diluents. Suitable aromatic hydrocarbon diluents are benzene, toluene, xylene, and other alkyl or halogen substituted aromatic compounds. Most preferably, the diluent is an aromatic hydrocarbon, especially toluene. After preparation in the foregoing manner the residual hydroxyl content thereof is desirably reduced to a level less than 1.0 meq of OH per gram of support, by any of the previously disclosed techniques.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

In general, the polymerization may be accomplished at conditions well known in the prior art for Ziegler-Natta or Kaminsky-Sinn type polymerization reactions, such as temperatures from 0°–250° C. and pressures from atmospheric to 1000 atmospheres (0.1 to 100 MPa). Suspension, solution, slurry, gas phase or other process conditions may be employed if desired. The support, if present, is preferably employed in an amount to provide a weight ratio of catalyst (based on metal):support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for polymerization via a solution process are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1,7-octadiene, 1-octene, 1-decene, styrene, divinylbenzene, ethylidenenorbornene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in the same or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

One such polymerization process comprises: contacting, optionally in a solvent, one or more α-olefins with a catalyst according to the present invention, in one or more continuous stirred tank or tubular reactors, or in the absence of solvent, optionally in a fluidized bed gas phase reactor, connected in series or parallel, and recovering the resulting polymer. Condensed monomer or solvent may be added to the gas phase reactor as is well known in the art.

In another process an ethylene/α-olefin interpolymer composition is prepared by:

(A) contacting ethylene and at least one other α-olefin under polymerization conditions in the presence of a catalyst composition of the present invention in at least one reactor to produce a first interpolymer or optionally a solution of a first interpolymer, (B) contacting ethylene and at least one other α-olefin under polymerization conditions and at a higher polymerization reaction temperature than used in step (A) in the presence of a heterogeneous Ziegler catalyst in at least one other reactor to produce a second interpolymer optionally in solution, and (C) combining the first interpolymer and second interpolymer to form an ethylene/α-olefin interpolymer blend composition, and (D) recovering the ethylene/α-olefin interpolymer blend composition.

Preferably the heterogeneous Ziegler catalyst comprises:

(i) a solid support component comprising magnesium halide, silica, modified silica, alumina, aluminum phosphate, or a mixture thereof, and (ii) a transition metal component represented by the formula:

wherein:

Tr is a Group 4, 5, or 6 metal, u is a number from 0 to 6 that is less than or equal to v, v is the formal oxidation number of Tr, X" is halogen, and R'" independently each occurrence is a hydrocarbyl group having from 1 to 20 carbon atoms.

These polymerizations are generally carried out under solution conditions to facilitate the intimate mixing of the two polymer-containing streams. The foregoing technique allows for the preparation of ethylene/α-olefin interpolymer compositions having a broad range of molecular weight distribution and composition distribution. Preferably, the heterogeneous catalyst is also chosen from those catalysts which are capable of efficiently producing the polymers under high temperature, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition of the present invention to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:

(i) a solid support component comprising a magnesium halide or silica, and (ii) a transition metal component represented by the formula:

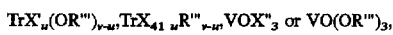

wherein:

Tr, X'', u, v, and R''' are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{4-8}$ α-olefins, most desirably 1-octene.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

EXAMPLES

Materials and Methods

Unless otherwise stated, all chemical manipulations were performed under nitrogen in either an inert atmosphere glove box or on a nitrogen/vacuum double manifold using standard Schelenk techniques.

Example 1

Preparation of $Me_4CpSi(Me)(OiPr)(N^tBu))Me_2$
Preparation of $MeSi(OiPr)(N^tBu)Cl$ To 45 ml (0.38 moles) of trichloromethylsilane in 1.5 L of anhydrous ether cooled at 0° C. in an ice bath was added 51.5 ml (0.38 moles) of triethylamine followed by dropwise addition of 29.5 ml (0.38 moles) of 2-propanol. After stirring for 4 hr, the precipitated white solid (triethylamine hydrochloride) was removed by filtration through a filter stick and washed with 2×100 ml portions of ether. The ether filtrate and washing as were then combined, cooled at 0° C. in an ice bath and 51.5 ml (0.38 moles) of triethylamine added followed by dropwise addition of 40.5 ml (0.38 moles) of t-butylamine. After stirring for a further four hours the resulting white slurry was again filtered, washed and the ether removed under vacuum to yield 70 g of MeSi(OiPr)(NH$^t$Bu)Cl (90 percent yield) as a clear colorless oil pure by gas chromatography.

b) Preparation of $Me_4CpHSi(Me)(OiPr)(NH^tBu)$

To 13 g (0.062 moles) of MeSi(OiPr)(NH$^t$Bu)Cl dissolved in 500 ml of tetrahydrofuran was added 10 g (0.062 moles) of potassium tetramethylcyclopentadienide over a 1 hr period. The mixture was brought to reflux and then stirred at room temperature for 4 hr. The orange slurry was filtered, and the solvent removed to yield 16.5 g of a yellow oil. This oil was then vacuum distilled and 13.3 g of product collected between 81°–85° C. as a light yellow oil (73 percent yield).

c) Preparation of $[Me_4CpSi(Me)(OiPr)(N^tBu)][MgCl]_2$

To 4.73 g (0.016 moles of $Me_4CpHSi(Me)(OiPr)(NH^tBu)$ in 45 ml of toluene was added 14.5 ml of a 2.2M solution of isopropyl-magnesium chloride in ether. After stirring for 20 minutes, the ether was removed under vacuum and the remaining toluene solution refluxed for 3 hr. To the warm solution was added 0.5 ml of dimethoxyethane at which point a gelatinous solid precipitated. The remaining solvent was decanted off and hexane added to the remaining mass which was triturated and refluxed. The hexane was then decanted off and the remaining solid dried under vacuum to give 6.5 g of a white solid (94 percent yield). To 0.2 g of this solid was added 10 ml of 4.5M $H_2SO_4$ and 20 ml of distilled water. After shaking for 2 hr the solid had dissolved and the hydrolysate made up to 100 ml and chloride and magnesium content determined by $AgNO_3$ and EDTA titration respectively.

d) Preparation of $(Me_4CpSi(Me)(OiPr)(N^tBu))TiCl_2$

To 2 g (0.00465 moles) of $[Me_4CpSi(Me)(OiPr)(N^tBu)][MgCl]_2$ in 100 ml of dimethoxyethane was slowly added 1.45 g (0.00465 moles) of $TiCl_3(DME)_{1.75}$ over a 30 min period. After further stirring for 15 min the mixture turned a dark brown color at which point 1.5 ml (0.019 moles) of anhydrous chloroform was added. After five minutes the solution had turned a dark orange color. The solvent was then removed under vacuum and the remaining dark orange solid recrystallized from n-pentane at −37° C. to yield 1.1 g of a crystalline orange solid (57 percent yield).

e) Preparation of $(Me_4CpSi(Me)(OiPr)(N^tBu))TiMe_2$

To 25 ml of diethylether was added 0.190 g (0.466 mmol) of $(Me_4CpSi(Me)(OiPr)(N^tBu))TiCl_2$. To this solution 0.337 ml (1.01 mmol) of a 3.0M diethyl ether solution of methylmagnesium iodide was added dropwise. After the addition was complete the resulting solution was stirred for 40 minutes. The solvent was then removed under reduced pressure and the residue extracted with hexane, filtered and the solvent removed via vacuum to give 0.081 g of product (47 percent yield).

Example 2

Preparation of $Me_4CpSi(Me)(O-2-Bu)(N^tBu)TiMe_2$ a) Preparation of $MeSi(O-2Bu)(NH^tBu)Cl$ To 62.8 ml (0.54 moles) of trichloromethylsilane in 1.5 L of anhydrous tetrahydrofuran cooled at 0° C. in an ice bath was added 71.5 ml (0.54 moles) of triethylamine followed by dropwise addition of 49 ml (0.54 moles) of 2-butanol. After stirring for 4 hr, the precipitated white solid (triethylamine hydrochloride) was removed by filtration through a filter stick and washed with 2×100 ml portions of tetrahydrofuran. The filtrate and washings as were then combined, cooled at 0° C. in an ice bath and 71.5 ml (0.54 moles) of triethylamine added followed by dropwise addition of 56.3 ml (0.54 moles) of t-butylamine. After stirring for a further four hours the resulting white slurry was again filtered, washed and the solvent removed under vacuum to yield 120 g of MeSi(O-2Bu)(NHtBu)Cl (94 percent yield) as a clear colorless oil pure by gas chromatography.

b) Preparation of Me4CpHSi(Me)(O2-Bu)(NHtBu)

To 14 g (0.062 moles) of MeSi(O-2Bu)(NH$^t$Bu)Cl dissolved in 300 ml of tetrahydrofuran was added 10 g (0.062 moles) of potassium tetramethylcyclopentadienide over a 1 hr period. The mixture was brought to reflux and then stirred at room temperature for 4 hr. The orange slurry was filtered, and the solvent removed to yield 16 g of a yellow oil. This oil was then vacuum distilled and 13.8 g of product collected between 98°–110° C. as a light yellow oil (72 percent yield).

c) Preparation of [Me$_4$CpSi(Me)(O-2Bu)(N$^t$Bu)][MgCl]$_2$

To 5 g (0.016 moles) of Me$_4$CpHSi(Me)(O-2Bu)(NH$^t$Bu) in 45 ml of toluene was added 14.5 ml of a 2.2M solution of isopropyl-magnesium chloride in ether. After stirring for 20 minutes, the ether was removed under vacuum and the remaining toluene solution refluxed for 3 hr. To the warm solution was added 0.5 ml of dimethoxyethane at which point a gelatinous solid precipitated. The remaining solvent was decanted off and hexane added to the remaining mass which was triturated and refluxed. The hexane was then decanted off and the remaining solid dried under vacuum to give 6 g a white solid (94 percent yield). To 0.2 g of this solid was added 10 ml of 4.5M H$_2$SO$_4$ and 20 ml of distilled water. After shaking for 2 hr the solid had dissolved and the hydrolysate made up to 100 ml and chloride and magnesium content determined by AgNO$_3$ and EDTA titration respectively.

d) Preparation of (Me$_4$CpSi(Me)(O-2Bu)(N$^t$Bu)TiCl$_2$

To 2.5 g (0.00465 moles) of [Me$_4$CpSi(Me)(O-2Bu)(N$^t$Bu)][MgCl]$_2$ in 100 ml of dimethoxyethane was slowly added 1.45 g (0.00465 moles) of TiCl$_3$(DME)1.75 over a 30 min period. After further stirring for 15 min the mixture turned a dark brown color at which point 1.5 ml (0.019 moles) of anhydrous chloroform. After 5 minutes the solution had turned a dark orange color. The solvent was then removed under vacuum and the remaining solid extracted with n-pentane to yield 0.9 g of a dark orange oil (45 percent yield).

e) Preparation of (Me$_4$CpSi(Me)(O-2Bu)(N$^t$Bu))TiMe$_2$

To 20 mL of diethylether was added 1.22 g (2.86 mmol) of (Me$_4$CpSi(Me)(O-2Bu)(N$^t$Bu))TiMe$_2$. To this solution 1.90 ml (5.72 mmol) of a 3.0M diethylether solution of methylmagnesium iodide was added dropwise. After the addition was complete the resulting solution was stirred for 40 minutes. The solvent was then removed under reduced pressure and the residue extracted with hexane, filtered and the solvent removed via vacuum to give 1.00 g of product (90 percent yield).

Example 3

Preparation of Me$_4$CpSi(Me)(OEt)(N$^t$Bu)TiCl$_2$ a) Preparation of MeSi(OEt)(NH$^t$Bu)Cl To 62.8 ml (0.54 moles) of trichloromethylsilane in 1.5 L of anhydrous ether cooled at 0° C. in an ice bath was added 71.5 ml (0.54 moles) of triethylamine followed by dropwise addition of 32 ml (0.54 moles) of ethanol. After stirring for 4 hr, the precipitated white solid (triethylamine hydrochloride) was removed by filtration through a filter stick and washed with 2×100 ml portions of tetrahydrofuran. The filtrate and washings as were then combined, cooled at 0° C. in an ice bath and 71.5 ml (0.54 moles) of triethylamine added followed by dropwise addition of 56.3 ml (0.54 moles) of t-butylamine. After stirring for a further four hours the resulting white slurry was again filtered, washed and the solvent removed under vacuum to yield 100 g of MeSi(OEt)(NH$^t$Bu)Cl (94 percent yield) as a clear colorless oil which was only 46 percent pure by gas chromatography. The remaining fractions were 13 percent of the diethoxy monoamine, 8 percent of the monoethoxydiamine adduct and 23 percent of the dichloromonoamine adduct.

The oil was then vacuum distilled and 38 g of a fraction boiling between 40° and 65° C. collected and found to have a GC/MS consistent with MeSi(OEt)(NH$^t$Bu)Cl.

b) Preparation of Me$_4$CpSi(Me)(OEt)(N$^t$Bu)

To 10 g (0.051 moles) of Preparation of MeSi(OEt)(NH$^t$Bu)Cl dissolved in 300 ml of tetrahydrofuran was added 7 g (0.046 moles) of potassium tetramethylcyclopentadienide over a 1 hr period. The mixture was brought to reflux and then stirred at room temperature for 12 hr. The orange slurry was filtered, and the solvent removed to yield 12 g of a yellow oil. This oil was then vacuum distilled and 7 g of product collected between 45°–70° C. as a light yellow oil (49 percent yield).

c) Preparation of [Me$_4$CpSi(Me)(OEt)(N$^t$Bu)][MgCl]$_2$

To 3.4 g (0.012 moles) of Me$_4$CpSi(Me)(OEt)(N$^t$Bu) in 45 ml of toluene was added 0.55 ml (0.0067 moles) of tetrahydrofuran and the mixture heated to 85° C. The heating was then terminated and 11.3 ml of a 2.2M solution of isopropylmagnesium chloride in ether (0.025 moles) added over 15 minutes. The slurry was then refluxed overnight cooled to room temperature and 0.88 ml of tetrahydrofuran added followed by 30 ml of hexane. After stirring overnight, a white powder precipitated which was filtered off and dried in vacuo, to give 1.32 g a white solid. To 0.2 g of this solid was added 10 ml of 4.5M H2SO4 and 20 ml of distilled water. After shaking for 2 hr the solid had dissolved and the hydrolysate made up to 100 ml and chloride and magnesium content determined by AgNO$_3$ and EDTA titration respectively.

d) Preparation of (Me$_4$CpSi(Me)(OEt)(N$^t$Bu))TiCl$_2$

To 1.45 g (0.0047 moles) of TiCl$_3$(DME)$_{1.75}$ in 100 ml of dimethoxyethane was slowly added 3.5 g (0.0047 moles) of [Me$_4$CPSi(Me)(OEt)(N$^t$Bu)][MgCl]$_2$ over a 30 min period. After further stirring for 15 min the mixture turned a dark brown color at which point 1.5 ml (0.019 moles) of anhydrous dichloromethane was added. After five minutes the solution had turned a dark orange color. The solvent was then removed under vacuum and the remaining dark orange solid recrystallized from n-pentane at −37° C. to yield 0.9 g of a crystalline orange solid (45 percent yield).

Polymerization

A two-liter Parr reactor was charged with 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). 2.0 μmol each of catalyst and cocatalyst at 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. Results are contained in Table 1.

TABLE 1

| Run | Complex | Cocatalyst | efficiency[2] |
|---|---|---|---|
| 1 | Ex. 1 | TPFPB[1] | 1,025,000 |
| 2 | Ex. 2 | " | 1,280,000 |

[1] trispentafluorophenylborane
[2] g polymer/g titanium

What is claimed is:

1. A metal complex corresponding to the formula:

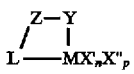

or a dimer, solvated adduct, chelated derivative or mixture thereof,
wherein:

L is a delocalized, π-bonded group that is bound to M, containing up to 50 nonhydrogen atoms;

M is a metal of Group 3, 4 or the Lanthanide series of the Periodic Table of the Elements;

Z is a covalently bound, divalent substituent of up to 50 non-hydrogen atoms having the formula, —(ER$_2$)$_m$—, wherein E independently each occurrence is carbon, silicon or germanium, R independently each occurrence is selected from the group consisting of $C_{1-20}$ hydrocarbyl, and $C_{1-20}$ hydrocarbyloxy, with the proviso that in at least one occurrence R is $C_{1-20}$ hydrocarbyloxy, and m is an integer from 1 to 3;

y is a divalent ligand group comprising nitrogen, phosphorus, oxygen or sulfur, said Y containing up to 20 nonhydrogen atoms;

X' is a neutral Lewis base ligand having up to 20 non-hydrogen atoms;

X" independently each occurrence is a monovalent, anionic moiety selected from hydride, halo, hydrocarbyl, silyl, germyl, hydrocarbyloxy, amide, siloxy, halohydrocarbyl, halosilyl, silylhydrocarbyl, and aminohydrocarbyl having up to 20 non-hydrogen atoms, or two X" groups together form a divalent hydrocarbadiyl group;

n is a number from 0 to 3; and p is an integer from 0 to 2.

2. A metal complex according to claim 1 corresponding to the formula:

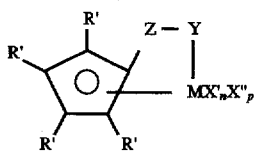

wherein:

M is titanium, zirconium or hafnium, preferably titanium, in the +2, +3 or +4 formal oxidation state;

—Z—Y— is as previously defined in claim 1;

R' independently in each occurrence is selected from the group consisting of hydrogen, hydrocarbyl, silyl, germyl, cyano, halo and combinations thereof, said R' having up to 20 non-hydrogen atoms each, or adjacent R' groups together form a divalent derivative that is a hydrocarbadiyl, siladiyl or germadiyl group;

X' is a conjugated diene having from 4 to 30 non-hydrogen atoms, which forms a π-complex with M when M is in the +2 formal oxidation state, whereupon n is 1 and p is 0;

X" each occurrence is an anionic ligand group that is covalently bonded to M when M is in the +3 or +4 formal oxidation state, whereupon n is 0 and p is 1 or 2, and optionally two X" groups together for a divalent anionic ligand group, whereupon n is 0; or a dimer, solvated adduct, chelated derivative or mixture thereof.

3. A metal complex according to claim 2 wherein R' independently in each occurrence is selected from the group consisting of hydrogen, methyl, ethyl, and all isomers of propyl, butyl, pentyl and hexyl, as well as cyclopentyl, cyclohexyl, norbornyl, benzyl, and trimethyl silyl; or adjacent R' groups are linked together thereby forming a fused ring system, or a dimer, solvated adduct, chelated derivative or mixture thereof.

4. A complex according to claim 1, wherein X' is $\eta^4$-1, 4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; or $\eta^4$-1,4-bis(trimethylsilyl)-1,3-butadiene, or a dimer, solvated adduct, chelated derivative or mixture thereof.

5. A complex according to claim 1, wherein X" is chloride, methyl, benzyl, phenyl, tolyl, t-butyl, methoxide, or trimethylsilyl or two X" groups together are 1,4-butanediyl, s-cis(1,3-butadiene), or s-cis(2,3-dimethyl-1,3-butadiene), or a dimer, solvated adduct, chelated derivative or mixture thereof.

6. A complex according to claim 1, wherein E is silicon, m is 1, and R in at least one occurrence is methoxide, ethoxide, propoxide or butoxide, or a dimer, solvated adduct, chelated derivative or mixture thereof.

7. A complex according to claim 1 wherein Y is —NR*—, wherein R* is $C_{1-10}$ hydrocarbyl, or a dimer, solvated adduct, chelated derivative or mixture thereof.

8. A complex according to claim 7 wherein R* is methyl, ethyl, propyl, butyl, pentyl, hexyl, (including branched and cyclic isomers), norbornyl, 2,4,6-trimethylphenyl, 1-adamantanyl, benzyl, or phenyl, or a dimer, solvated adduct, chelated derivative or mixture thereof.

9. A complex according to claim 1 wherein L is cyclopentadienyl, tetramethylcyclopentadienyl, indenyl, tetrahydroindenyl, fluorenyl, tetrahydrofluorenyl, octahydrofluorenyl, or one of the foregoing groups further substituted with one or more methyl, ethyl, propyl, butyl, pentyl, hexyl, (including branched and cyclic isomers), norbornyl, benzyl, or phenyl groups, or a dimer, solvated adduct, chelated derivative or mixture thereof.

10. A catalyst system comprising a metal complex according to claim 1 and an activating cocatalyst.

11. A supported catalyst system comprising a catalyst system according to claim 10 and an aluminum or silicon containing substrate.

12. A process for polymerizing an α-olefin, comprising contacting an α-olefin or a mixture of α-olefins with a catalyst system according to claim 10 or 11.

* * * * *

UNITED STATES PATENT AND TRADEMARK OFFICE
CERTIFICATE OF CORRECTION

PATENT NO : 5,688,880

DATED : Novmeber 18, 1997

INVENTOR(S) : Lee Spencer et al.

It is certified that error appears in the above-identified patent and that said Letters Patent is hereby corrected as shown below:

Claim 2, column 29, line 48, delete "preferably titanium,"

Claim 2, column 30, line 2, "together for a divalent" should correctly read --together form a divalent--.

Signed and Sealed this

Twenty-fourth Day of October, 2000

Attest:

Q. TODD DICKINSON

*Attesting Officer*          *Director of Patents and Trademarks*